United States Patent [19]
Parce et al.

[11] Patent Number: 5,779,868
[45] Date of Patent: Jul. 14, 1998

[54] ELECTROPIPETTOR AND COMPENSATION MEANS FOR ELECTROPHORETIC BIAS

[75] Inventors: J. Wallace Parce, Palo Alto; Michael R. Knapp, Aptos, both of Calif.

[73] Assignee: Caliper Technologies Corporation, Palo Alto, Calif.

[21] Appl. No.: 671,986

[22] Filed: Jun. 28, 1996

[51] Int. Cl.$^6$ .......................... G01N 27/26; G01N 27/447
[52] U.S. Cl. .......................... 204/604; 204/451; 204/453; 204/454; 204/601
[58] Field of Search .................................. 204/451, 452, 204/453, 454, 455, 601, 602, 603, 604, 605

[56] References Cited

U.S. PATENT DOCUMENTS

| | | | |
|---|---|---|---|
| 4,908,112 | 3/1990 | Pace | 210/198.2 |
| 4,963,498 | 10/1990 | Hillman et al. | 436/69 |
| 5,126,022 | 6/1992 | Soane et al. | 204/458 |
| 5,140,161 | 8/1992 | Hillman et al. | 250/341.3 |
| 5,144,139 | 9/1992 | Hillman et al. | 250/341.3 |
| 5,164,598 | 11/1992 | Hillman et al. | 250/341.3 |
| 5,188,963 | 2/1993 | Stapleton | 435/288.3 |
| 5,192,405 | 3/1993 | Petersen et al. | 204/451 |
| 5,302,264 | 4/1994 | Welch et al. | 204/452 |
| 5,304,487 | 4/1994 | Wilding et al. | 435/29 |
| 5,486,335 | 1/1996 | Wilding et al. | 422/58 |
| 5,498,392 | 3/1996 | Wilding et al. | 422/68.1 |
| 5,560,811 | 10/1996 | Briggs et al. | 204/451 |
| 5,571,410 | 11/1996 | Swedberg et al. | 210/198.2 |
| 5,593,838 | 1/1997 | Zanzucchi et al. | 435/6 |
| 5,605,662 | 2/1997 | Heller et al. | 422/68.1 |
| 5,630,925 | 5/1997 | Pentoney, Jr. et al. | 204/604 |

FOREIGN PATENT DOCUMENTS

| | | | |
|---|---|---|---|
| 4-160356 | 6/1992 | Japan | 204/604 |
| 9405414 | 3/1994 | WIPO . | |
| 9604547 | 2/1996 | WIPO . | |
| WO 96/29595 | 9/1996 | WIPO . | |
| 9702357 | 1/1997 | WIPO . | |

OTHER PUBLICATIONS

Dasgupta, Purnendu K. et al., "Electroosmosis: A Reliable Fluid Propulsion System for Flow Injection Analysis", Anal. Chem., 1994, 66, 1792-1798.

Linhares, Michael C. et al., "Use of an On-Column Fracture in Capillary Zone Electrophoresis for Sample Introduction", Anal. Chem., 1991, 63, 2076-2078.

S. Jacobson et al., "Effects of injection schemes and column geometry on the performance of microchip electrophoresis devices," Anal. Chem. 66:1107-1113.

S. Jacobson et al., "High-speed separations on a microchip," Anal. Chem. 66:1114-1118 (1994).

S. Jacobson et al., "Fused quartz substrates for microchip electrophoresis," Anal. Chem. 67:2059-2063 (1995).

S. Jacobson et al., "Open channel electrochromatography on a microchip," Anal. Chem. 66:2369-2373 (1994).

(List continued on next page.)

*Primary Examiner*—Donald R. Valentine
*Assistant Examiner*—John S. Starsiak, Jr.
*Attorney, Agent, or Firm*—Townsend and Townsend and Crew LLP

[57] ABSTRACT

The present invention provides for techniques for transporting materials using electrokinetic forces through the channels of a microfluidic system. The materials are transported in slug regions of high ionic concentration, next to buffer material regions of high ionic concentration, which are separated by buffer material regions of low ionic concentration. Such arrangements allow the materials to remain localized for the transport transit time to avoid mixing of the materials. Using these techniques, an electropipettor which is compatible with the microfluidic system is created so that materials can be easily introduced into the microfluidic system. The present invention also compensates for electrophoretic bias as materials are transported through the channels of the microfluidic system by splitting a channel into portions with positive and negative surface charges and a third electrode between the two portions, or by diffusion of the electrophoresing materials after transport along a channel.

12 Claims, 6 Drawing Sheets

OTHER PUBLICATIONS

S. Jacobson et al., "Precolumn reactions with electrophoretic analysis integrated on a microchip," *Anal. Chem.* 66:4127–4132 (1994).

S. Jacobson et al., "Microchip electrophoresis with sample stacking," *Electrophoresis* 16:481–486 (1995).

A. Manz et al., "Electroosmotic pumping and electrophoretic separations for miniaturized chemical analysis systems," *J. Micromech. Microeng.* 4:257–265 (1994).

J. Ramsey et al., "Microfabricated chemical measurement systems," *Nature Medicine* 1(10):1093 (Oct., 1995).

K. Seiler et al., "Electroosmotic pumping and valveless control of fluid flow within a manifold of capillaries on a glass chip," *Anal. Chem.* 66:3485–3491 (1994).

Bao et al., "Ultramicro enzyme assays in a capillary electrophoretic system", J. Chromatog., 608: 212–224 (1992).

Effenhauser, et al., "Glass Chips for High-Speed Capillary Electrophoresis Separations with Submicrometer Plate Heights", Anal. Chem., 1993, 65, 2637–2642.

Fan et al., "Micromachining of Capillary Electrophoresis Injectors and Separators on Glass Chips and Evaluation of Flow at Capillary Intersections", Anal. Chem., 66, 177–184 (1994).

Harmon et al., "Mathematical Treatment of Electrophoretically Mediated Microanalysis", Anal. Chem., 65, 2655–2662, 1993.

Harmon, et al., "Selectively in Electrophoretically Mediated Microanalysis by Control of Product Detection Time", Anal. Chem., 66, 3797–3805, 1994.

Harrison, et al., "Capillary Electrophoresis and Sample Injection Systems Integrated on a Planar Glass Chip", Anal. Chem., 64, 1926–1932, 1992.

Harrison et al., "Micromachining a Miniaturized Capillary Electrophoresis–Based Chemical Analysis System on a Chip", Science, vol. 261, 895–897, (1993).

Manz et al., "Planar chips technology for miniaturization and integration of separation techniques into monitoring systems", J. Chromat., 593, 253–258, (1992).

Manz et al., "Miniaturized Total Chemical Analysis Systems: a Novel Concept for Chemical Sensing", Sensors & Actuators, B1, 244–248, (1990).

Manz et al., "Micromachining of monocrystalline silicon and glass for chemical analysis systems, A look into next century's technology or just a fashionable craze?", Trends in Anal. Chem. vol. 10, No. 5, 1991, 144–149.

Seiler, et al., "Planar Glass Chips for Capillary Electrophoresis: Repetitive Sample Injection, Quantitation, and Separation Efficiency", Anal. Chem., 1993, 65, 1481–1488.

ELECTROPIPETTOR AND COMPENSATION MEANS FOR ELECTROPHORETIC BIAS

BACKGROUND OF THE INVENTION

There has been a growing interest in the manufacture and use of microfluidic systems for the acquisition of chemical and biochemical information. Techniques commonly associated with the semiconductor electronics industry, such as photolithography, wet chemical etching, etc., are being used in the fabrication of these microfluidic systems. The term, "microfluidic", refers to a system or device having channels and chambers which are generally fabricated at the micron or submicron scale, e.g., having at least one cross-sectional dimension in the range of from about 0.1 µm to about 500 µm. Early discussions of the use of planar chip technology for the fabrication of microfluidic systems are provided in Manz et al., *Trends in Anal. Chem.* (1990) 10(5):144–149 and Manz et al., *Avd. in Chromatog.* (1993) 33:1–66, which describe the fabrication of such fluidic devices and particularly microcapillary devices, in silicon and glass substrates.

Applications of microfluidic systems are myriad. For example, International Pat. Appln. WO 96/04547, published Feb. 15, 1996, describes the use of microfluidic systems for capillary electrophoresis, liquid chromatography, flow injection analysis, and chemical reaction and synthesis. Companion patent application, U.S. Appln. Ser. No. 08/761,575 (Attorney Docket No. 17646-400), entitled "HIGH THROUGHPUT SCREENING ASSAY SYSTEMS IN MICROSCALE FLUIDIC DEVICES", filed of even date by J. Wallace Parce et al. and assigned to the present assignee, discloses wide ranging applications of microfluidic systems in rapidly assaying large number of compounds for their effects on chemical, and preferably, biochemical systems. The phrase, "biochemical system," generally refers to a chemical interaction which involves molecules of the type generally found within living organisms. Such interactions include the full range of catabolic and anabolic reactions which occur in living systems including enzymatic, binding, signalling and other reactions. Biochemical systems of particular interest include, e.g., receptor-ligand interactions, enzyme-substrate interactions, cellular signalling pathways, transport reactions involving model barrier systems (e.g., cells or membrane fractions) for bioavailability screening, and a variety of other general systems.

Many methods have been described for the transport and direction of fluids, e.g., samples, analytes, buffers and reagents, within these microfluidic systems or devices. One method moves fluids within microfabricated devices by mechanical micropumps and valves within the device. See, Published U.K. Patent Application No. 2 248 891 (Oct. 18, 1990), Published European Patent Application No. 568 902 (May 2, 1992), U.S. Pat. Nos. 5,271,724 (Aug. 21, 1991) and 5,277,556 (Jul. 3, 1991). See also, U.S. Pat. No. 5,171,132 (Dec. 21, 1990) to Miyazaki et al. Another method uses acoustic energy to move fluid samples within devices by the effects of acoustic streaming. See, Published PCT Application No. 94/05414 to Northrup and White. A straightforward method applies external pressure to move fluids within the device. See, e.g., the discussion in U.S. Pat. No. 5,304,487 to Wilding et al.

Still another method uses electric fields to move fluid materials through the channels of the microfluidic system. See, e.g., Published European Patent Application No. 376 611 (Dec. 30, 1988) to Kovacs, Harrison et al., *Anal. Chem.* (1992) 64:1926–1932 and Manz et al. *J. Chromatog.* (1992) 593:253–258. U.S. Pat. No. 5,126,022 to Soane. Electrokinetic forces have the advantages of direct control, fast response and simplicity. However, there are still some disadvantages. For maximum efficiency, it is desirable that the subject materials be transported as closely together as possible. Nonetheless, the materials should be transported without cross-contamination from other transported materials. Further, the materials in one state at one location in a microfluidic system should remain in the same state after being moved to another location in the microfluidic system. These conditions permit the testing, analysis and reaction of the compound materials to be controlled, when and where as desired.

In a microfluidic system in which the materials are moved by electrokinetic forces, the charged molecules and ions in the subject material regions and in the regions separating these subject material regions are subjected to various electric fields to effect fluid flow.

Upon application of these electric fields, however; differently charged species within the subject material will exhibit different electrophoretic mobilities, i.e., positively charged species will move at a different rate than negatively charged species. Where simple fluid transport is desired, these varied mobilities can result in an undesirable alteration or "electrophoretic bias" in the subject material.

Without consideration and measures to avoid cross-contamination, the microfluidic system must either widely separate the subject materials, or, in the worst case, move the materials one at a time through the system. In either case, efficiency of the microfluidic system is markedly reduced. Furthermore, if the state of the transported materials cannot be maintained in transport, then many applications which require the materials to arrive at a location unchanged must be avoided.

The present invention solves or substantially mitigates these problems of electrokinetic transport. With the present invention, microfluidic systems can move materials efficiently and without undesired change in the transported materials. The present invention presents a high throughput microfluidic system having direct, fast and straightforward control over the movement of materials through the channels of the microfluidic system with a wide range of applications, such as in the fields of chemistry, biochemistry, biotechnology, molecular biology and numerous other fields.

SUMMARY OF THE INVENTION

The present invention provides for a microfluidic system which electroosmotically moves subject material along channels in fluid slugs from a first point to a second point in the microfluidic system. A buffer region of high ionic concentration contacts each slug on at least one side and buffer regions of low ionic concentration are arranged with the slugs and high ionic concentration buffer regions so that at least one low ionic concentration region is always between the first and second points to ensure that most of the voltage drop and resulting electric field between the two points is across the low ionic concentration region.

The present invention also provides for a electropipettor which is compatible with a microfluidic system which moves subject materials with electroosmotic forces. The electropipettor has a capillary having a channel. An electrode is attached along the outside length of the capillary and terminates in a electrode ring at the end of the capillary. By manipulating the voltages on the electrode and the electrode at a target reservoir to which the channel is fluidly connected when the end of the capillary is placed into a material source, materials are electrokinetically introduced into the channel. A train of subject material slugs, high and low ionic concentration buffer regions can be created in the channel for easy introduction into the microfluidic system.

The present invention further compensates for electrophoretic bias as the materials are electrokinetically transported along the channels of a microfluidic system. In one embodiment a channel between two points of the microfluidic system has two portions with sidewalls of opposite surface charges. An electrode is placed between the two portions. With the voltages at the two points substantially equal and the middle electrode between the two portions set differently, electrophoretic forces are in opposite directions in the two portions, while electroosmotic forces are in the same direction. As subject material is transported from one point to the other, electrophoretic bias is compensated for, while electroosmotic forces move the fluid materials through the channel.

In another embodiment a chamber is formed at the intersection of channels of a microfluidic system. The chamber has sidewalls connecting the sidewalls of the intersecting channels. When a slug of subject material is diverted from one channel into another channel at the intersection, the chamber sidewalls funnel the slug into the second channel. The width of the second channel is such that diffusion mixes any subject material which had been electrophoretically biased in the slug as it travelled along the first channel.

DETAILED DESCRIPTION OF THE INVENTION

General Organization of a Microfluidic System

Figure 1:
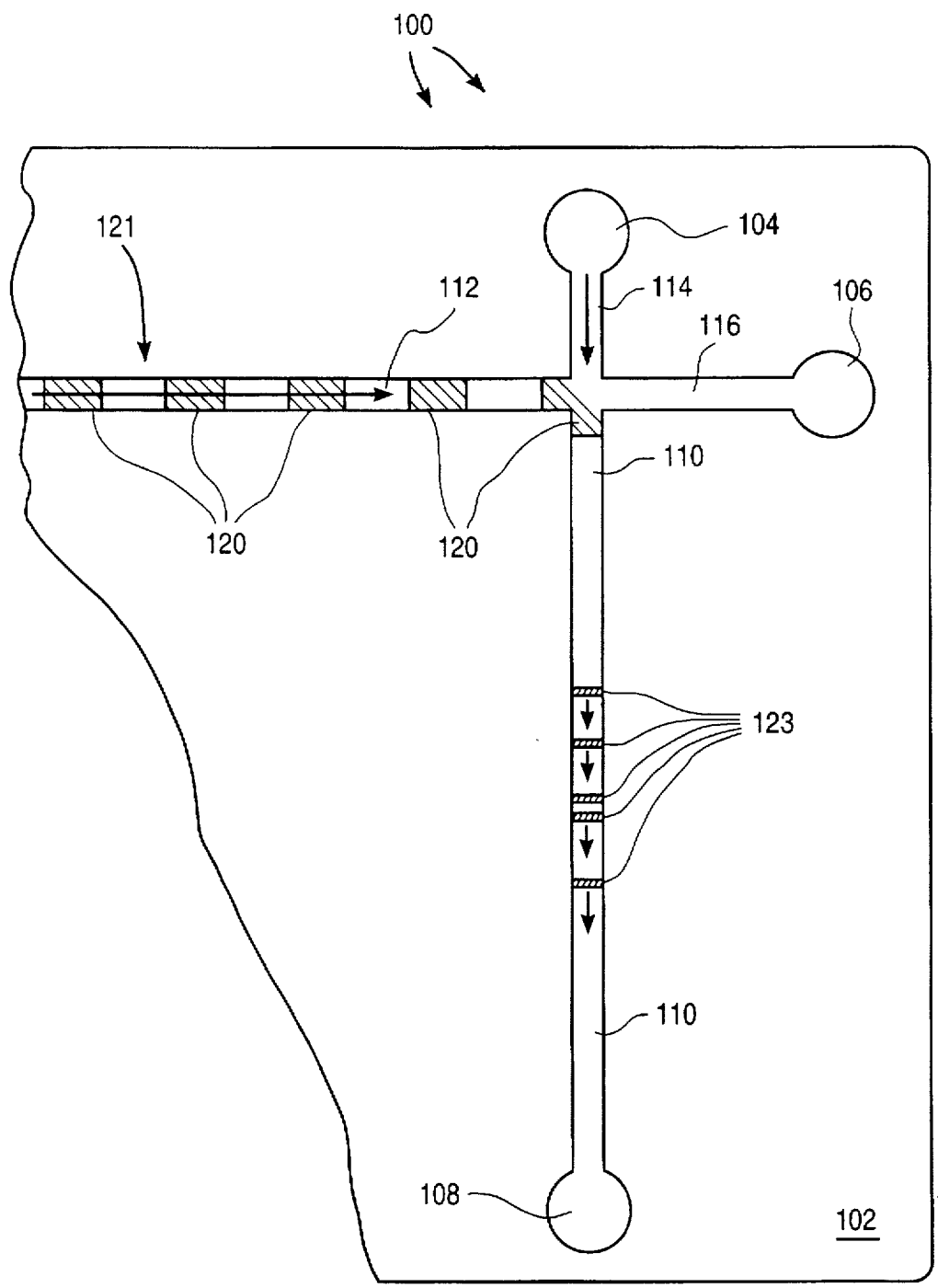
FIG. 1 shows a schematic illustration of one embodiment of a microfluidic system.

FIG. 1 discloses a representative diagram of an exemplary microfluidic system 100 according to the present invention. As shown, the overall device 100 is fabricated in a planar substrate 102. Suitable substrate materials are generally selected based upon their compatibility with the conditions present in the particular operation to be performed by the device. Such conditions can include extremes of pH, temperature, ionic concentration, and application of electrical fields. Additionally, substrate materials are also selected for their inertness to critical components of an analysis or synthesis to be carried out by the system.

Useful substrate materials include, e.g., glass, quartz and silicon, as well as polymeric substrates, e.g., plastics. In the case of conductive or semiconductive substrates, there should be an insulating layer on the substrate. This is particularly important where the device incorporates electrical elements, e.g., electrical fluid direction systems, sensors and the like, or uses electroosmotic forces to move materials about the system, as discussed below. In the case of polymeric substrates, the substrate materials may be rigid, semi-rigid, or non-rigid, opaque, semi-opaque or transparent, depending upon the use for which they are intended. For example, devices which include an optical or visual detection element, will generally be fabricated, at least in part, from transparent materials to allow, or at least, facilitate that detection. Alternatively, transparent windows of, e.g., glass or quartz, may be incorporated into the device for these types of detection elements. Additionally, the polymeric materials may have linear or branched backbones, and may be crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate and the like.

The system shown in FIG. 1 includes a series of channels 110, 112, 114 and 116 fabricated into the surface of the substrate 102. As discussed in the definition of "microfluidic," these channels typically have very small cross sectional dimensions, preferably in the range of from about 0.1 μm to about 100 μm. For the particular applications discussed below, channels with depths of about 10 μm and widths of about 60 μm work effectively, though deviations from these dimensions are also possible.

Manufacturing of these channels and other microscale elements into the surface of the substrate 102 may be carried out by any number of microfabrication techniques that are well known in the art. For example, lithographic techniques may be employed in fabricating glass, quartz or silicon substrates, for example, with methods well known in the semiconductor manufacturing industries. Photolithographic masking, plasma or wet etching and other semiconductor processing technologies define microscale elements in and on substrate surfaces. Alternatively, micromachining methods, such as laser drilling, micromilling and the like, may be employed. Similarly, for polymeric substrates, well known manufacturing techniques may also be used. These techniques include injection molding techniques or stamp molding methods where large numbers of substrates may be produced using, e.g., rolling stamps to produce large sheets of microscale substrates, or polymer microcasting techniques where the substrate is polymerized within a microfabricated mold.

Besides the substrate 102, the microfluidic system includes an additional planar element (not shown) which overlays the channeled substrate 102 to enclose and fluidly seal the various channels to form conduits. The planar cover element may be attached to the substrate by a variety of means, including, e.g., thermal bonding, adhesives or, in the case of glass, or semi-rigid and non-rigid polymeric substrates, a natural adhesion between the two components. The planar cover element may additionally be provided with access ports and/or reservoirs for introducing the various fluid elements needed for a particular screen.

The system 100 shown in FIG. 1 also includes reservoirs 104, 106 and 108, which are disposed and fluidly connected at the ends of the channels 114, 116 and 110 respectively. As shown, sample channel 112, is used to introduce a plurality of different subject materials into the device. As such, the channel 112 is fluidly connected to a source of large numbers of separate subject materials which are individually introduced into the sample channel 112 and subsequently into another channel 110. As shown, the channel 110 is used for analyzing the subject materials by electrophoresis. It should be noted that the term, "subject materials," simply refers to the material, such as a chemical or biological compound, of interest. Subject compounds may include a wide variety of different compounds, including chemical compounds, mixtures of chemical compounds, e.g., polysaccharides, small organic or inorganic molecules, biological macromolecules, e.g., peptides, proteins, nucleic acids, or extracts made from biological materials, such as bacteria, plants, fungi, or animal cells or tissues, naturally occurring or synthetic compositions.

The system 100 moves materials through the channels 110, 112, 114 and 116 by electrokinetic forces which are provided by a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple independent voltage sources may be used. The voltage controller is electrically connected to each of the reservoirs via an electrode positioned or fabricated within each of the plurality of reservoirs. See, for example, published International Patent Application No. WO 96/04547 to Ramsey, which is incorporated herein by reference in its entirety for all purposes.

Electrokinetic Transport

The electrokinetic forces on the fluid materials in the channels of the system 100 may be separated into electroosmotic forces and electrophoretic forces. The fluid control systems used in the system of the present invention employ electroosmotic force to move, direct and mix fluids in the various channels and reaction chambers present on the surface of the substrate 102. In brief, when an appropriate fluid is placed in a channel or other fluid conduit having functional groups present at the surface, those groups can ionize. Where the surface of the channel includes hydroxyl functional groups at the surface, for example, protons can leave the surface of the channel and enter the fluid. Under such conditions, the surface possesses a net negative charge, whereas the fluid possesses an excess of protons or positive charge, particularly localized near the interface between the channel surface and the fluid.

By applying an electric field across the length of the channel, cations flow toward the negative electrode. Movement of the positively charged species in the fluid pulls the solvent with them. The steady state velocity of this fluid movement is generally given by the equation:

$$v = \frac{\epsilon \xi E}{4\pi\eta}$$

where v is the solvent velocity, $\epsilon$ is the dielectric constant of the fluid, $\xi$ is the zeta potential of the surface, E is the electric field strength, and $\eta$ is the solvent viscosity. Thus, as can be easily seen from this equation, the solvent velocity is directly proportional to the zeta potential and the applied field.

Besides electroosmotic forces, there are also electrophoretic forces which affect charged molecules as they move through the channels of the system 100. In the transport of subject materials from one point to another point in the system 100, it is often desirable for the composition of the subject materials to remain unaffected in the transport, i.e., that the subject materials are not electrophoretically differentiated in the transport.

In accordance with the present invention, the subject materials are moved about the channels in slugs, which have a high ionic concentration to minimize electrophoretic forces on the subject materials in the slugs. To minimize the effect of electrophoretic forces upon the subject materials in the slugs, buffer regions, or "guard bands" are placed on either side of a slug. These buffer regions have a high ionic concentration to minimize the electric fields in these regions, as explained below, so that subject materials are essentially unaffected by the transport from one location to another location in a microfluidic system. The subject materials are transported through the representative channels 110, 112, 114, 116 of the system 100 in regions of certain ionic strengths, together with other regions of ionic strengths varying from the regions bearing the subject materials.

Figure 2A:
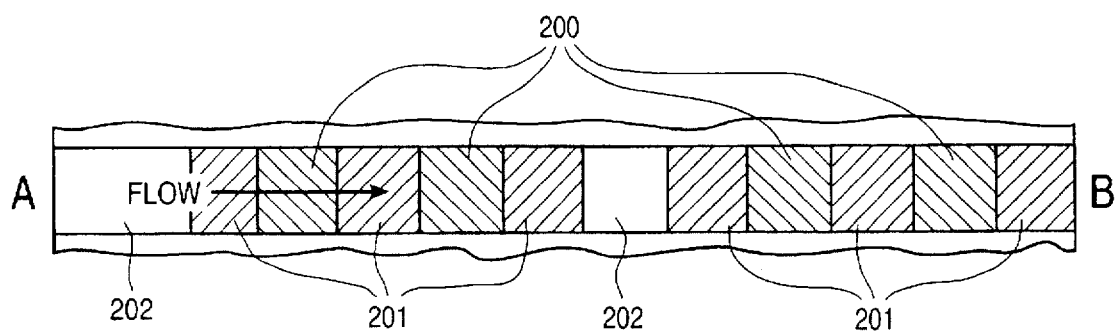
FIG. 2A illustrates an arrangement of fluid regions travelling in a channel of the microfluidic system of FIG. 1, according to one embodiment of the present invention.

A specific arrangement is illustrated in FIG. 2A, which illustrates subject materials in plugs 200 being transported from point A to point B along a channel of the microfluidic system 100. In either side of the plugs 200 are buffer regions 201 of high ionic strength. Additionally, buffer regions 202 of low ionic concentration periodically separate arrangements of plugs 200 and buffer regions 201. Being of low ionic concentration, most of the voltage drop between points A and B occurs across these regions 202. The low concentration regions 202 are interspersed between the arrangements of slug 200 and region 201 such that, as the slugs 200 and the regions 201 are electroosmotically pumped through the channel, there is always at least one low ionic concentration buffer region 202 between the points A and B. This ensures that most of the voltage drop occurs in the region 202, rather than across the slug 200 and buffer regions 201. Stated differently, the electric field between points A and B is concentrated in the region 202 and the slugs 200 and buffer regions 201 experience low electric fields (and low electrophoretic forces). Thus, depending upon the relative ionic concentrations in the slugs 200, buffer regions 201 and low ionic concentration regions 202, other arrangements of these slugs 200, buffer regions 201 and 202 can be made.

Figure 2B:
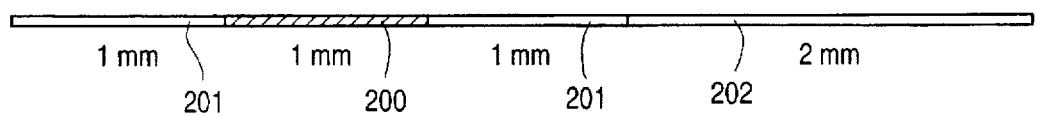
FIG. 2B is a scaled drawing of another arrangement of fluid regions travelling in a channel of the microfluidic system according to the present invention.

For example, FIG. 2B illustrates an arrangement in which a low concentration buffer region 202 is regularly spaced between each combination of buffer region 201/slug 200/buffer region 201. Such an arrangement ensures that there is always at least one low concentration buffer region 202 between points A and B. Furthermore, the drawings are drawn to scale to illustrate the relative lengths of a possible combination of slug 200, high concentration buffer region 201 and low concentration buffer region 202. In the example of FIG. 2B, the slug 200 holds the subject material in a high ionic concentration of 150 mM of NaCl. The slug 200 is 1 mm long in the channel. The two high concentration buffer regions 201 have ionic concentrations of 150 mM of NaCl. Each region 201 is 1 mm long. The low concentration buffer region 202 is 2 mm and has an ionic concentration of 5 mM of borate buffer. This particular configuration is designed to maintain a rapidly electrophoresing compound, such as benzoic acid, for example, in the slug 200 and buffer regions 201 for 72 seconds as the compound travels through the channels of the microfluidic system.

Stated more generally, the velocity of fluid flow, $v_{EoF}$, through the channels of the microfluidic system can be determined and, by measurement, it is possible to determine the total distance, $l_T$, which a subject matter molecule is to travel through the channels. Thus the transit time, $t_{Tr}$, for the subject matter molecule to travel the total distance is:

$$t_{Tr} = l_T / V_{EoF}$$

To contain a subject matter molecule x within the buffer region 201 next to the slug 200, the length of the buffer region 201, $l_g$, should be greater than the electrophoretic velocity of the subject matter molecule x in the region 201, $v_{gx}$, multiplied by the transit time:

$$l_g > (v_{gx})(t_{Tr})$$

Since the electrophoretic velocity is proportional to the electric field in the buffer region 201, the present invention allows control over $v_{gx}$ so that the subject matter can be contained in transport through the microfluidic system channels.

In the arrangements in FIGS. 2A and 2B, the high concentration buffer regions 201 help maintain the position of the subject material in the vicinity of its slug 200. No matter what the polarity of the charges of the subject material, the buffer regions 201 on either side of the slug 200 ensures that any subject material leaving the slug 200 is only subject to a low electric field due to the relative high ionic concentrations in the buffer regions 201. If the polarity of the subject material is known, then the direction of the electrophoretic force on the molecules of the subject material is also known.

Figure 3A:
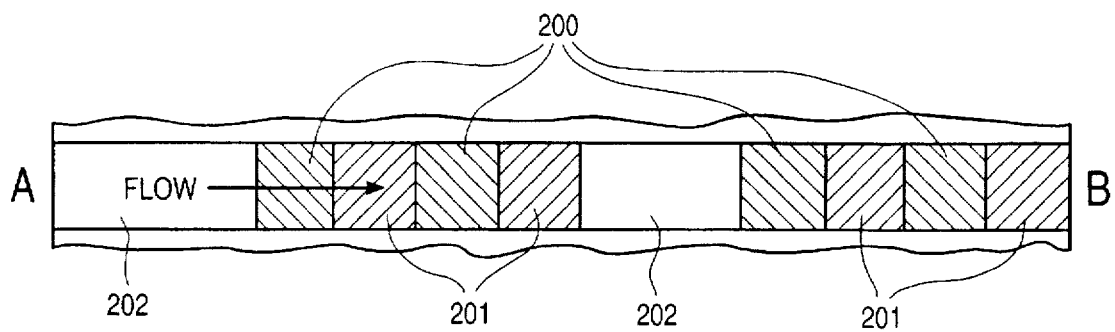
FIG. 3A is another arrangement with high ionic concentration buffer regions before a slug travelling within a channel of the microfluidic system.

FIG. 3A illustrates an example where charges of the subject material in all the slugs 200 are such that the electrophoretic force on the subject matter molecules are in the same direction as the direction of the electroosmotic flow. Hence the buffer regions 201 precede the slugs 200 in the direction of flow. There are no buffer regions 201 following the slugs 200 because the electrophoretic force keeps the subject material from escaping the slug 200 in that direction. By eliminating one-half of the buffer regions 201, more slugs 200 with their subject material can be carried per channel length. This enhances the transportation efficiency of the microfluidic system. The low ionic concentration buffer regions 202 are arranged with respect to the slugs 200 and high ionic concentration buffer regions 201 so that high electric fields fall in the regions 202 and the electric fields (and electrophoretic forces) in the slugs 200 and buffer regions 201 are kept low.

Figure 3B:
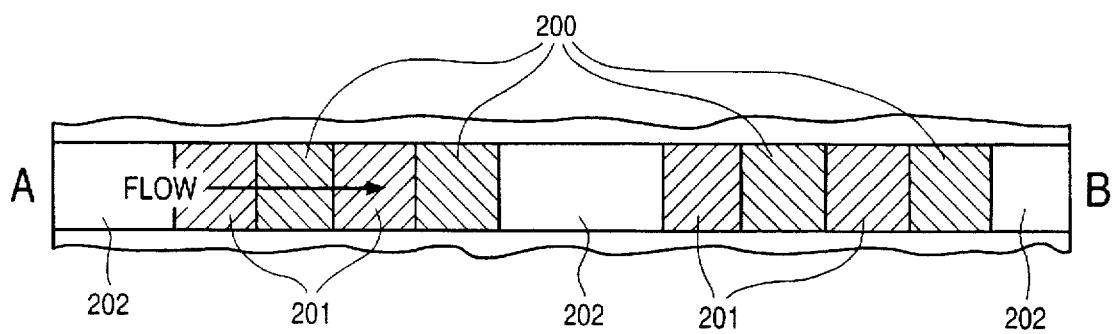
FIG. 3B shows an arrangement with high ionic concentration buffer regions after a slug travelling in a channel of the microfluidic system.

In FIG. 3B the buffer regions 201 follow the slugs 200 in the direction of the electroosmotic flow. In this example, the charges of the subject material in all the slugs 200 are such that the electrophoretic force on the subject matter molecules are in the opposite direction as the direction of the electroosmotic flow. Hence the subject material may escape by, in effect, being left behind by its slug 200. The buffer regions 201 following the slugs 200 keep the subject material from migrating too far from its slug 200. Likewise, the low ionic concentration buffer regions 202 are arranged with the slugs 200 and high ionic concentration buffer regions 201 so that high electric fields fall in the regions 202 and the electric fields in the slugs 200 and buffer regions 201 are kept low.

Various high and low ionic strength solutions are selected to produce a solution having a desired electrical conductivity for the buffer regions 201 and 202. The specific ions that impart electrical conductivity to the solution may be derived from inorganic salts (such as NaCl, KI, $CaCl_2$, $FeF_3$, $(NH_4)_2SO_4$ and so forth), organic salts (such as pyridinium benzoate, benzalkonium laurate), or mixed inorganic/organic salts (such as sodium benzoate, sodium deoxylsulfate, benzylaminehydrochloride). These ions are also selected to be compatible with the chemical reactions, separations, etc. to be carried out in the microfluidic system. In addition to aqueous solvents, mixtures of aqueous/organic solvents, such as low concentrations of DMSO in water, may be used to assist in the solubilization of the subject matter molecules. Mixtures of organic solvents, such as $CHCl_3$:MeOH, may be also used for the purpose of accelerating assays for phospholipase activity, for example.

Generally, when aqueous solvents are used, solution conductivity is adjusted using inorganic ions. When less polar solvents are used, organic or mixed inorganic/organic ions are typically used. In cases where two immiscible solvents may be simultaneously present (e.g., water and a hydrocarbon such as decane) such that electrical current must flow from one into the other, ionophores (e.g., valinomycin, nonactin, various crown ethers, etc.) and their appropriate ions may be used to conduct current through the non-polar solvent.

Electropipettor

As described above, any subject material can be transported efficiently through the microfluidic system 100 in or near the slugs 200. With the buffer regions 201 and 202, the subject materials are localized as they travel through the channels of the system. For efficient introduction of subject matter into a microfluidic system, the present invention also provides an electropipettor which introduces subject material into a microfluidic system in the same serial stream of combinations of slug 200, buffer regions 201 and 202.

Figure 4A:
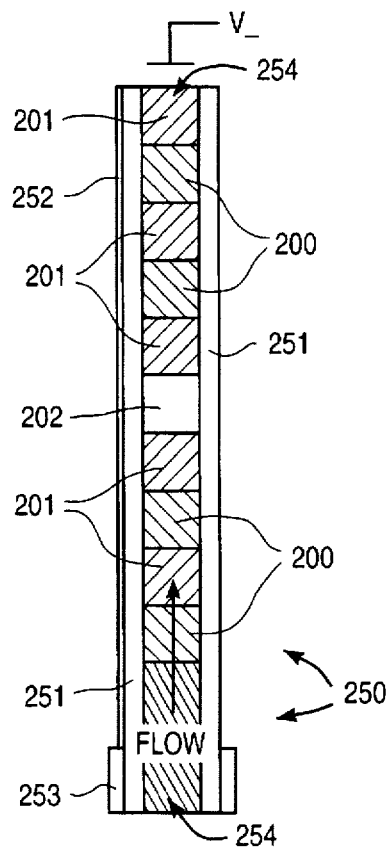
FIG. 4A is a schematic diagram of one embodiment of a electropipettor according to the present invention.

As illustrated in FIG. 4A, an electropipettor 250 is formed by a hollow capillary tube 251. The capillary tube 251 has a channel 254 with the dimensions of the channels of the microfluidic system 100 to which the channel 254 is fluidly connected. As shown in FIG. 4A, the channel 254 is a cylinder having a cross-sectional diameter in the range of 1–100 µm, with a diameter of approximately 30 µm being preferable. An electrode 252 runs down the outside wall of the capillary tube 251 and terminates in a ring electrode 253 around the end of the tube 251. To draw the subject materials in the slugs 200 with the buffer regions 201 and 202 into the electropipettor channel 254, the electrode 252 is driven to a voltage with respect to the voltage of a target reservoir (not shown) which is fluidly connected to the channel 254. The target reservoir is in the microfluidic system 100 so that the slugs 200 and the buffer regions 201 and 202 already in the channel 254 are transported serially from the electropipettor into the system 100.

Procedurally, the capillary channel end of the electropipettor 250 is placed into a source of subject material. A voltage is applied to the electrode 252 with respect to an electrode in the target reservoir. The ring electrode 253, being placed in contact with the subject material source, electrically biases the source to create a voltage drop between the subject material source and the target reservoir. In effect, the subject material source and the target reservoir become Point A and B in a microfluidic system. The subject material is electrokinetically introduced into the capillary channel 254 to create a slug 200. The voltage on the electrode 252 is then turned off and the capillary channel end is placed into a source of buffer material of high ionic concentration. A voltage is again applied to the electrode 252 with respect to the target reservoir electrode such that the buffer region 201 is electrokinetically introduced into the capillary channel 254 next to the slug 200. If a low ionic concentration buffer region 202 is then desirable in the electropipettor channel 254, the end of the capillary channel 254 is inserted into a source of low ionic concentration buffer material and a voltage applied to the electrode 252. The electropipettor 250 can then move to another source of subject material to create another slug 200 in the channel 254.

By repeating the steps above, a plurality of slugs 200 with different subject materials, which are separated by buffer regions 201 and 202, are electrokinetically introduced into the capillary channel 254 and into the microfluidic system 100.

Note that if the sources of the subject material and the buffer materials (of low and high ionic concentration) have their own electrode, the electrode 252 is not required. Voltages between the target reservoir and the source electrodes operate the electropipettor.

Figure 4B:
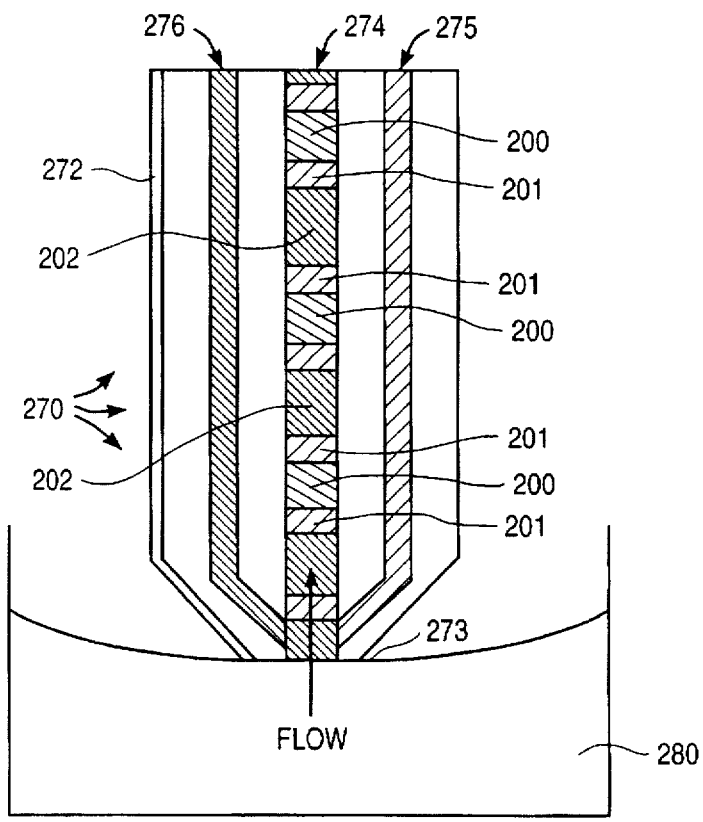
FIG. 4B is a schematic diagram of another electropipettor according to the present invention.
Figure 4C:
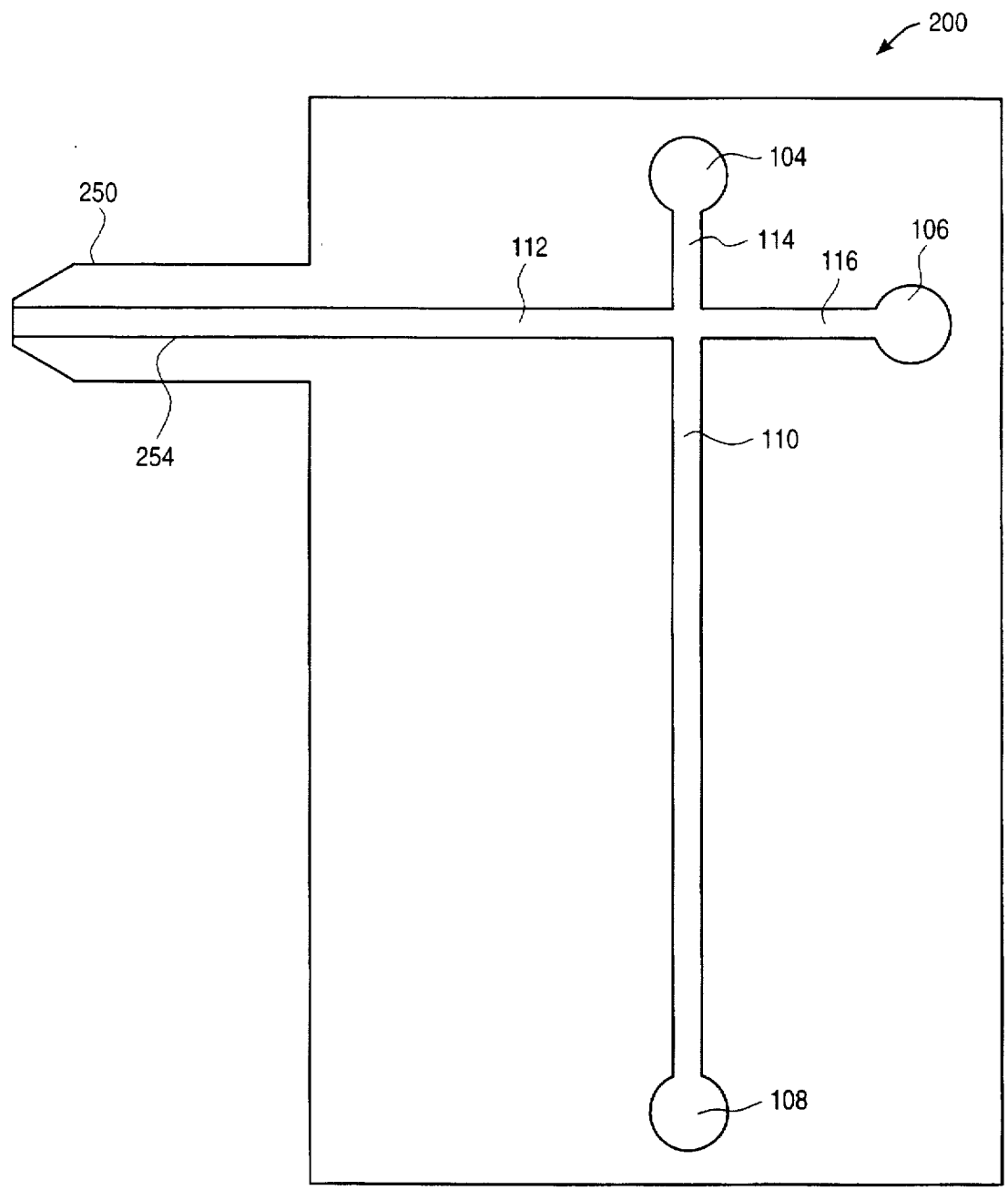
FIG. 4C illustrates the combination of the electropipettor with the microfluidic system.
Figure 6D:
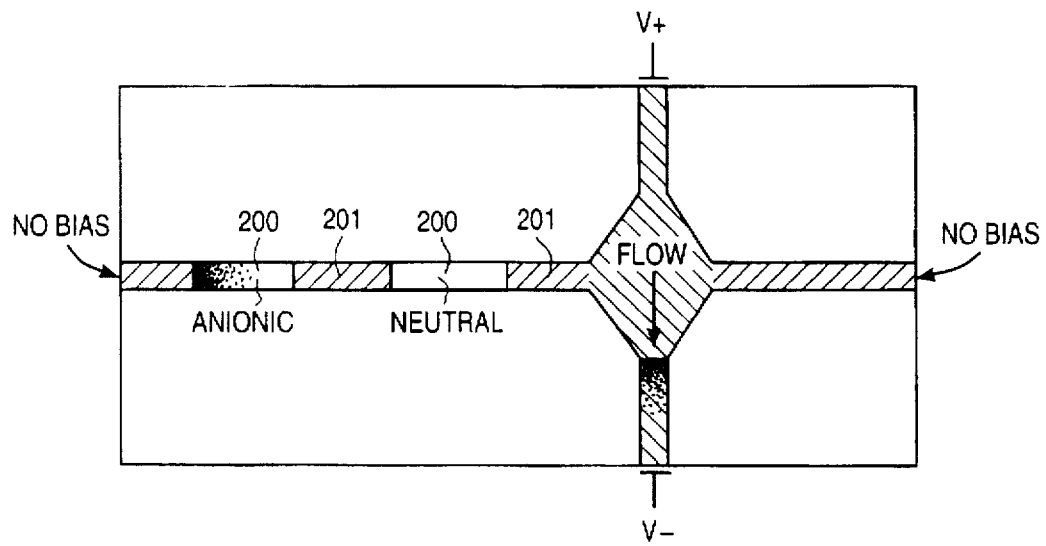
FIGS. 6A–6D illustrate the mixing action of funneling sidewalls at the intersection of channels in a microfluidic system, according to the present invention.

FIG. 4B illustrates a variation of the electropipettor 250 of FIG. 4A. In this variation the electropipettor 270 is not required to travel between a subject material source and buffer material sources to create the buffer regions 201 and 202. The electropipettor 270 has a body 271 with three capillary channels 274, 275 and 276. The main channel 274 operates identically to the channel 254 of the previously described electropipettor 250. However, the two auxiliary capillary channels 275 and 276 at one end are fluidly connected to buffer source reservoirs (not shown) and the other end of the channels 275 and 276 is fluidly connected to the main channel 274. One reservoir (say, the one connected to auxiliary channel 275) holds buffer material of high ionic concentration, and the other reservoir (connected to the channel 276) holds buffer material of low ionic concentration.

All of the reservoirs are connected to electrodes for electrically biasing these reservoirs for operation of the electropipettor 270. The electropipettor 270 may also have an electrode 272 along the walls of its body 271 which terminates in a ring electrode 273 at the end of the main channel 274. By applying voltages on the electrode 272 (and ring electrode 273) to create voltage drops along the channels 274, 275, 276, not only can subject material be drawn into the main channel 274 from subject material sources, but buffer material of high and low ionic concentrations can also be drawn from the auxiliary channels 275 and 276 into the main channel 274.

To operate the electropipettor 270 with the electrode 272, the end of the main capillary channel 274 is placed into a source 280 of subject material. A voltage is applied to the electrode 272 with respect to an electrode in the target reservoir to create a voltage drop between the subject material source 280 and the target reservoir. The subject material is electrokinetically drawn into the capillary channel 274. The capillary channel end is then removed from the subject material source 280 and a voltage drop is created between the target reservoir connected to the channel 274 and the reservoir connected to the channel 275. A high ionic strength buffer region 201 is formed in the channel 274. Capillary action inhibits the introduction of air into the channel 274 as the buffer material is drawn from the auxiliary channel 275. If a low ionic concentration buffer region 202 is then desired in the main channel 274, a voltage is applied to the electrodes in the target reservoir and in the reservoir of low ionic concentration buffer material. A buffer region 202 is electrokinetically introduced into the capillary channel 274 from the second auxiliary channel 276. The electropipettor 270 can then move to another source of subject material to create another slug 200 in the channel 274.

By repeating the steps above, a plurality of slugs 200 with different subject materials, which are separated by buffer regions 201 and 202, are electrokinetically introduced into the capillary channel 274 and into the microfluidic system 100.

If it is undesirable to subject the subject material source to oxidation/reduction reactions from the ring electrode 273, the electropipettor may be operated without the electrode 272. Because electroosmotic flow is slower in solutions of higher ionic strength, the application of a potential (− to +) from the reservoir connecting the channel 274 to the reservoir connecting the channel 275 results in the formation of a vacuum at the point where the channels 274 and 275 intersect. This vacuum draws samples from the subject material source into the channel 274. When operated in this mode, the subject material is somewhat diluted with the solutions in the channels 275 and 276. This dilution can be mitigated by reducing the relative dimensions of the channels 276 and 275 with respect to the channel 274.

To introduce buffer regions 201 and 202 into the capillary channel 274, the electropipettor 270 is operated as described above. The capillary channel end is removed from the subject material source 280 and a voltage drop is created between the target reservoir for the channel 274 and the reservoir connected to the selected channels 275 or 276.

Elimination of Electrophoretic Bias

As explained above, electrokinetic forces are used to transport the subject material through the channels of the microfluidic system 100. If the subject material is charged in solution, then it is subject to not only electroosmotic forces, but also to electrophoretic forces. Thus the subject material is likely to have undergone electrophoresis in travelling from one point to another point along a channel of the microfluidic system. Hence the mixture of the subject material or the localization of differently charged species in a slug 200 at the starting point is likely to be different than the mixture or localization at the arrival point. Furthermore, there is the possibility that the subject material might not even be in the slug 200 at the arrival point, despite the buffer regions 201.

Figure 5:
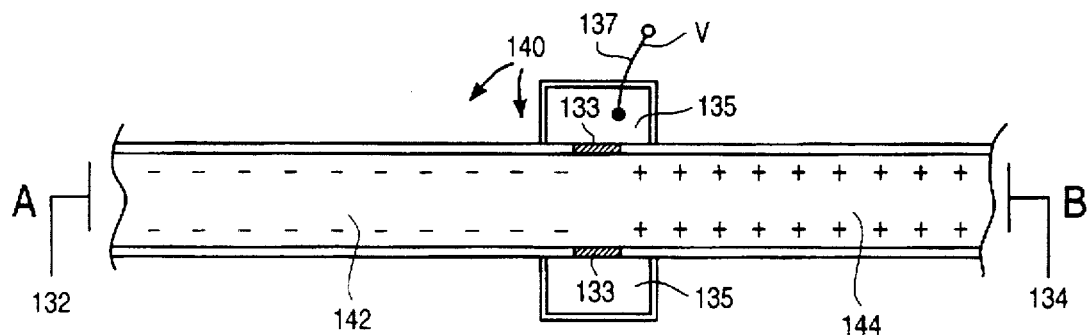
FIG. 5 is a schematic diagram of a channel having portions with oppositely charged sidewalls in a microfluidic system, according to the present invention.

Therefore, another aspect of the present invention compensates for electrophoretic bias as the subject materials are transported through the microfluidic system 100. One way to compensate for electrophoretic bias is illustrated in FIG. 5. In the microfluidic system 100 described above, each of the channels 110, 112, 114 and 116 was considered as a unitary structure along its length. In FIG. 5, an exemplary channel 140 is divided into two portions 142 and 144. The sidewalls of each channel portion 142 and 144 have surface charges which are of opposite polarity. The two channel portions 142 and 144 are physically connected together by a salt bridge 133, such as a glass frit or gel layer. While the salt bridge 133 separates the fluids in the channel 140 from an ionic fluid in a reservoir 135 which is partially defined by the salt barrier 133, the salt bridge 133 permits ions to pass through. Hence the reservoir 135 is in electrical, but not fluid, communication with the channel 140.

To impart electroosmotic and electrophoretic forces along the channel 140 between points A and B, electrodes 132 and 134 are arranged at points A and B respectively. Additionally, a third electrode 137 is placed in the reservoir 135 at the junction of the two portions 142 and 144. The electrodes 132 and 134 are maintained at the same voltage and the electrode 137 at another voltage. In the example illustrated in FIG. 5, the two electrodes 132 and 134 are at a negative voltage, while the electrode 137 and hence the junction of the two portions 142 and 144 are at zero voltage, i.e., ground. Thus the voltage drops, and hence the electric fields, in the portions 142 and 144 are directed in opposite directions. Specifically, the electric fields point away from each other. Thus the electrophoretic force on a particularly charged molecule is in one direction in the channel portion 142 and in the opposite direction in the channel portion 144. Any electrophoretic bias on a subject material is compensated for after travelling through the two portions 142 and 144.

The electroosmotic force in both portions 142 and 144 are still in the same direction, however. For example, assuming that the sidewalls of the channel portion 142 have positive surface charges, which attract negative ions in solution, and the sidewalls of the channel portion 144 have negative surface charges, which attract positive ions in solution, as shown in FIG. 5, the electroosmotic force in both portions 142 and 144 is to the right of the drawing. Thus the subject material is transported from point A to point B under electroosmotic force, while the electrophoretic force is in one direction in one portion 142 and in the opposite direction in the other portion 144.

To create a channel with sidewalls having positive or negative surface charges, one or both portions of the channel is coated with insulating film materials with surface charges, such as a polymer. For example, in the microfluidic system 100 the substrate 102 and the channels may be formed of glass. A portion of each channel is coated with a polymer of opposite surface charge, such as polylysine, for example, or is chemically modified with a silanizing agent containing an amino function, such as aminopropyltrichlorosilane, for example. Furthermore, the surface charge densities and volumes of both channel portions should be approximately the same to compensate for electrophoretic bias.

Rather than being formed in a solid planar substrate, the channel can also be formed by two capillary tubes which are butted together with a salt bridge which separates an ionic fluid reservoir from fluids in the capillary tubes. An electrode is also placed in the ionic fluid reservoir. One capillary tube has a negative surface charge and the other capillary tube a positive surface charge. The resulting capillary channel operates as described above.

FIGS. 6A–6D illustrates another embodiment of the present invention for which the effects of electrophoretic bias induced upon the subject material is moving from point A to point B are compensated. In this embodiment the subject material is mixed at point B, an intersection between two channels, such as illustrated in FIG. 1.

FIGS. 6A–6D show a chamber 160 is formed at the intersection of the channels 150, 152, 154 and 156. The chamber 160 has four sidewalls 162, 164, 166 and 168. The sidewall 162 connects a sidewall of the channel 152 to a sidewall of the channel 150; the sidewall 164 connects a sidewall of the channel 154 to the other sidewall of the channel 152; the sidewall 166 connects a sidewall of the channel 156 to the other sidewall of the channel 154; and the sidewall 168 connects the opposite sidewall of the channel 156 to the opposite sidewall of the channel 150. Assuming a flow of materials through the channel 152 toward the channel 156, the sidewalls 162 and 168 form as a funnel if the materials are diverted into the channel 150.

The dimensions of the sidewalls 162 and 168 accommodate the length of a subject material plug 200 travelling along the channel 152. The sidewalls 162 and 168 funnel down the plug 200 into the width of the channel 150. The width of the channel 150 is such that diffusion of the subject material occurs across the width of the channel 150, i.e., mixing occurs and any electrophoretic bias of the subject material created in the slug 200 travelling along the channel 162 is eliminated. For example, if the channel 150 is 50 μm wide, diffusion across the channel occurs in approximately one second for a molecule having a diffusion constant of $1 \times 10^{-5}$ cm$^2$/sec.

Figure 6A:
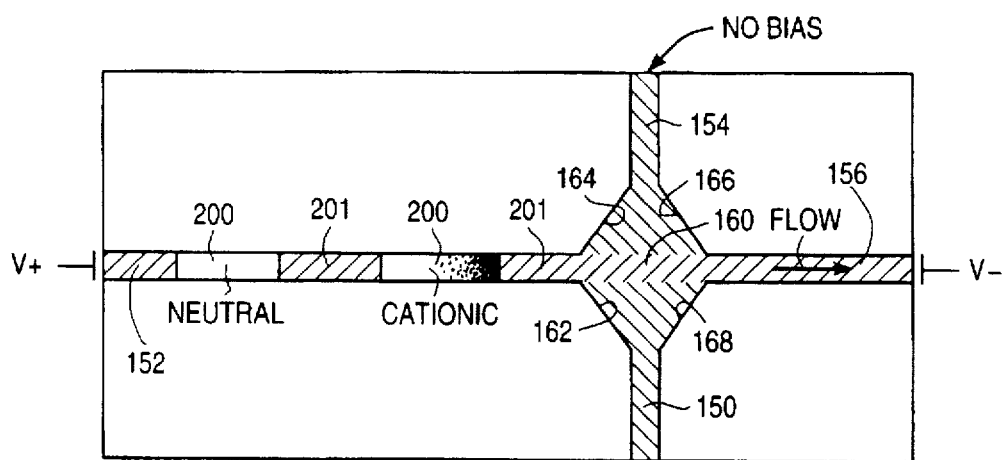
Figure 6B:
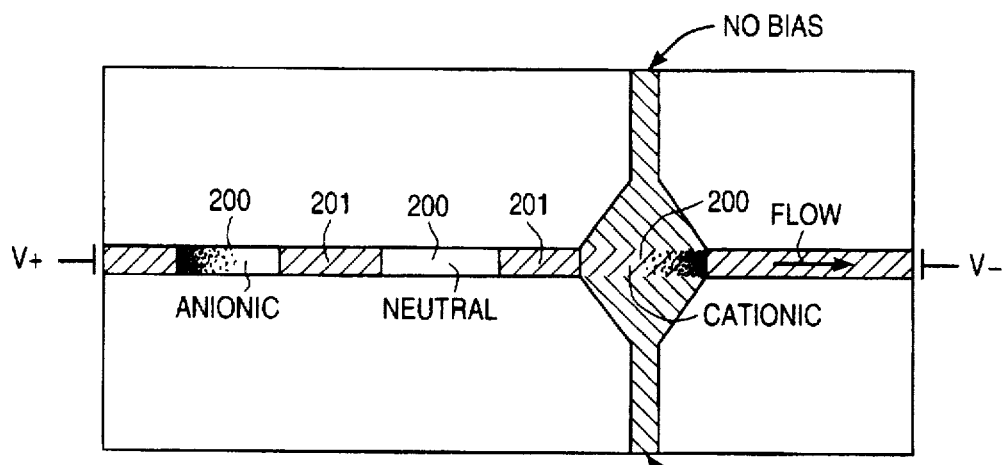
Figure 6C:
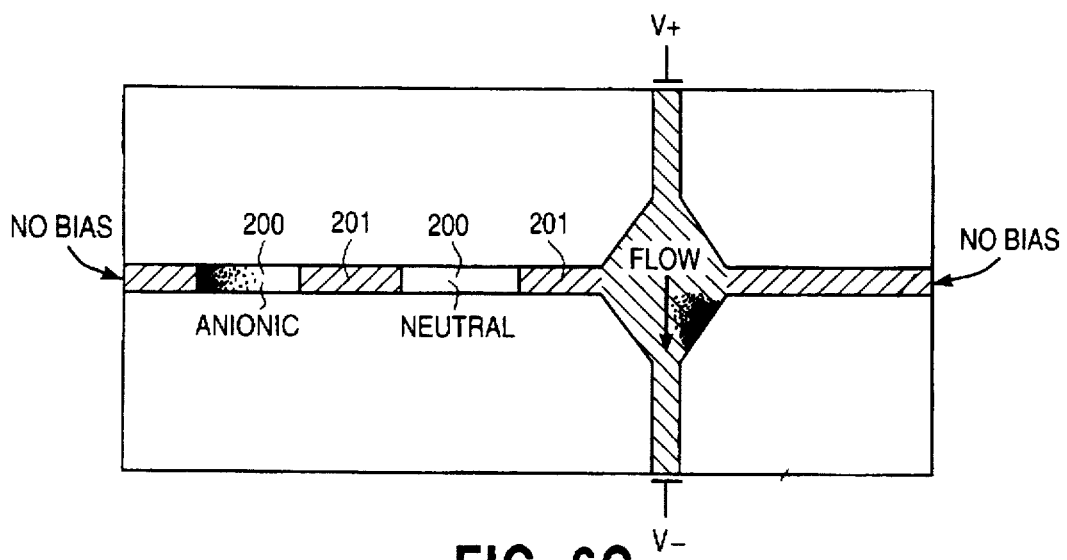

In FIG. 6A a plug 200 of cationic subject material is moving along the channel 152 towards the channel 156. By the time the plug 200 reaches the chamber 160, the subject material has undergone electrophoresis so that the material is more concentrated at the forward end of the slug 200. This is illustrated by FIG. 6B. Then the voltage drop impressed along the channels 152 and 156 is terminated and a voltage drop is created along the channels 154 and 150 to draw the slug 200 into the channel 150. The sidewalls 162 and 168 of the chamber 160 funnel the slug 200 with its electrophoretically biased subject material. This is illustrated by FIG. 6C. By diffusion the subject material is spread across the width of the channel 150 before the subject material travels any significant distance along the channel 150; the subject material in the slug 200 is mixed and ready for the next step of operation in the microfluidic system 100.

In addition to its use in correcting electrophoretic bias within a single sample, it will be appreciated that the structure shown in FIG. 6 will be useful in mixing fluid elements within these microfluidic devices, e.g., two distinct subject materials, buffers, reagents, etc.

While the foregoing invention has been described in some detail for purposes of clarity and understanding, it will be clear to one skilled in the art from a reading of this disclosure that various changes in form and detail can be made without departing from the true scope of the invention. For example, all the techniques described above may be used in various combinations. All publications and patent documents cited in this application are incorporated by reference in their entirety for all purposes to the same extent as if each individual publication or patent document were so individually denoted.

What is claimed is:

1. A combination comprising:

a microfluidic system comprising at least two intersecting channels disposed within a substrate;

an electropipettor for introducing materials into at least one of said at least two intersecting channels in said microfluidic system, said electropipettor comprising:

a body having a capillary channel therein, said capillary channel having a first end for contacting at least one source of said materials and a second end fluidly connected to at least one of said two intersecting channels in said microfluidic system; and a voltage source for applying a voltage between said one source of said materials and a first electrode in said microfluidic system when said capillary channel end contacts said one source of said materials such that material from said one source is electrokinetically introduced into said electropipettor toward said microfluidic system.

2. The combination of claim 1 wherein said capillary channel has a cross-sectional area of approximately 10–100 (μm)$^2$.

3. The combination of claim 1 wherein said voltage source applies a negative voltage to said first electrode with respect to said one source of materials.

4. A combination comprising a microfluidic system comprising at least one capillary channel disposed in a substrate;

an electropipettor for introducing materials into said at least one channel in said microfluidic system, said electropipettor comprising a first capillary channel in a body, said first capillary channel having a first end for contacting at least one source of subject materials and a second end fluidly connected to said microfluidic system;

a second capillary channel in said body, said second capillary channel having a first end terminating near said first end of said first capillary channel and a second end terminating in a source of first spacer material; and a voltage source for applying voltages between said at least one subject material source and said microfluidic system, and between said first spacer material source and said microfluidic system such that subject material from said one subject material source and spacer material from said first spacer material source are electrokinetically introduced into said electropipettor toward said microfluidic system.

5. The combination of claim 4 wherein said electropipettor further comprises a third capillary channel in said body, said third capillary channel having a first end terminating near said first end of said first capillary channel and a second end terminating in a source of second spacer material; and wherein said voltage source applies voltages to said second spacer material source and said microfluidic system such that subject material from said second spacer material source is electrokinetically introduced into said electropipettor toward said microfluidic system.

6. The combination of claim 5 wherein said first spacer material source holds spacer material of ionic concentration at least one order of magnitude greater than that of said second spacer material source.

7. The combination of claim 4 wherein said electropipettor further comprises an electrode disposed along said body such that said electrode contacts said subject material source when said first capillary channel end is placed into at least one source of said subject materials; and said voltage source is connected to said electrode to apply voltages between said at least one subject material source and said microfluidic system.

8. The combination of claim 1 wherein said electropipettor further comprises a second electrode at said first end of said capillary channel, said voltage source applying a voltage to said one source of said subject materials through said second electrode.

9. The combination of claim 8 wherein said second electrode is disposed along said body such that said second electrode contacts said subject material source when said capillary channel first end is contacted to said at least one source of said subject materials.

10. The combination of claim 2 wherein said capillary channel has a diameter of approximately 30 μm.

11. The combination of claim 4 wherein said first and second capillary channels have cross-sectional areas of approximately 10–1000 (μm)$^2$.

12. The combination of claim 11 wherein said first and second capillary channels have diameters of approximately 30 μm.

* * * * *